June 25, 1946. T. DOMOTO Plant Pat. 701
FLOWERING QUINCE PLANT
Filed June 23, 1945
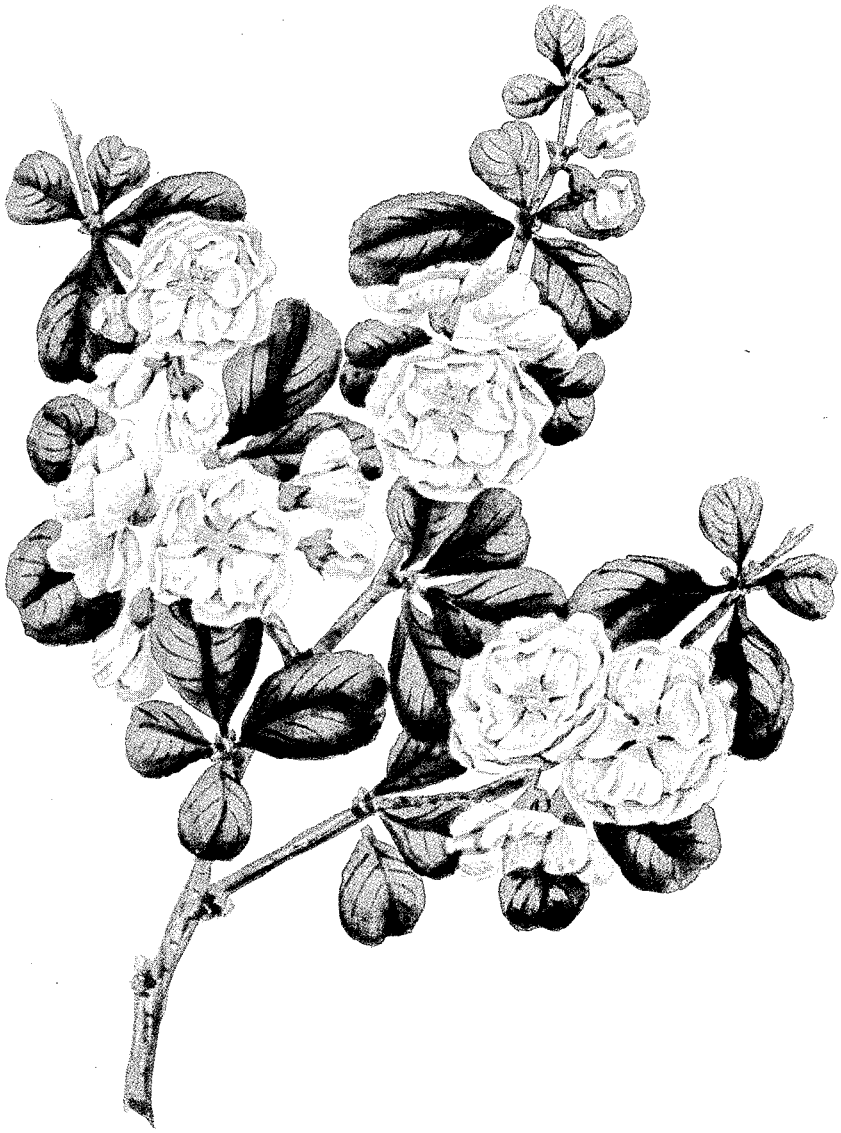
Inventor
Toichi Domoto
By: Rummler Rummler & Davis
Attys Patented June 25, 1946

Plant Pat. 701

UNITED STATES PATENT OFFICE

701

FLOWERING QUINCE PLANT

Toichi Domoto, Hayward, Calif.

Application June 23, 1945, Serial No. 601,198

1 Claim. (Cl. 47—60)

The present invention relates to a new and distinct variety of flowering quince plant, the successful result of definite breeding efforts to produce a semi-hardy, double-flowered, pure white untinged variety.

In 1935 at my greenhouse in Hayward, California, I commenced the breeding efforts that have resulted in my new variety, by crossing selected seedlings of *Chaenomeles japonica* and then through asexual propagation by cuttings, budding and grafting through several generations, these characteristics have been firmly fixed, thereby perpetuating the novel attributes in its progeny.

The primary objects in carrying out this invention were to develop and increase the uniformity of the pure white coloring of the flower and its doubleness of petals, which are largely the distinguishing characteristics of this new variety.

The accompanying illustration shows in full color a typical branch of full-blown blossoms.

The plant of this new variety is a shrub possessing great decorative value in its bushy habit of growth, its sturdy appearance and its distinctive blooms of pure white untinged color. Its branches support an abundance of leaves (which come out after the flowers) and its flowers form in axillary clusters at intervals along the stem. The flowers are distinctively large in size and double-petaled—the flowers of the ordinary single quince having but 5 petals whereas my new variety has from 10 to 20, the average number of petals being 15—and in form they are somewhat like the double-flowering peach. At a distance the general tonality of the flowers is pure white but an intimate view shows that each bloom has a contrasting yellow center. This new variety is a seasonal bloomer, coming into bloom in the spring and lasting from three weeks to a month.

I have found that there is no discoloration in the blooms under normal weather conditions.

This new variety is similar in plant structure to the ordinary flowering quince. The shrub is of medium height, 4 to 6 feet; its new foliage is the usual light green (Plate XXXII, color hue 32, tone i, Color Standards and Color Nomenclature, by Robert Ridgway, 1912) and the old foliage being a shade darker in tone. There is a faint shading of pink at the tip of the young leaves. The leaves have the usual size, texture and shape of the average flowering quince. Its spines are really tips of coming branches. Its stems are fairly smooth, and brown in color (Plate XLVI, color hue 14, i). The buds are of usual form and size and the flowers have the normal number of stamens and anthers, which are yellow in color, as is also the pollen.

My new variety is more resistant to fire-blight and its branches are more upright in appearance than "Double Carmen."

The following is a detailed description of my new variety:

Parentage: Seedling.
- *Seed parent.*—*Chaenomeles japonica.*
- *Botanic classification.*—*Chaenomeles Japonica.*
- *Form.*—Bushy.
- *Height.*—4 to 6 feet.
  - Spines at tips of branches.

*Flower*

Blooming habit: Seasonal.

Bloom:
- *Size.*—1½ inches to 2½ inches in diameter.
- *Borne.*—In axillary clusters (profuse bloomer).
- *Stems.*—Smooth and short; brown in color.
- *Petalage.*—10 to 20 petals.
- *Color.*—Pure white.
- *Discoloration.*—Under normal conditions, none.
- *Texture.*—Satin-like.
- *Affected by wet or hot weather.*—No.
- *Appearance.*—Like double-flowering peach.
- *Fragrance.*—None.
- *Disease resistance.*—Very good.
- *Lasting quality.*—On plant—excellent; as cut flower—good.

This new variety of flowering quince plant is easily distinguished from other varieties by its pure white coloring, fullness of bloom, and resistance to disease. These qualities combine to make a good commercial product. It is essentially an ornamental garden shrub but the blossoms have good-keeping qualities when used as cut flowers.

Having thus disclosed my invention, I claim:

A new and distinct variety of flowering quince plant with features in combination substantially as shown and described, characterized particularly by the double petalage of the flowers, its pure white untinted coloring, its resistance to disease, and its upright branch growth.

TOICHI DOMOTO.